United States Patent [19]

Schübert et al.

[11] Patent Number: 4,612,929
[45] Date of Patent: Sep. 23, 1986

[54] ATTACHMENT FOR THE SUPPLY OF BREATHING GAS FOR HIGH-FREQUENCY ARTIFICIAL RESPIRATION

[75] Inventors: Ernst W. Schübert, Lubeck; Peter Gebhardt, Stockelsdorf, both of Fed. Rep. of Germany

[73] Assignee: Drägerwerk AG, Fed. Rep. of Germany

[21] Appl. No.: 693,014

[22] Filed: Jan. 18, 1985

[30] Foreign Application Priority Data

Jan. 20, 1984 [DE] Fed. Rep. of Germany ....... 3401924

[51] Int. Cl.$^4$ ............................................ A61M 16/00
[52] U.S. Cl. ................................. 128/204.25; 128/912
[58] Field of Search ................... 128/204.25, 205.19, 128/207.15, 207.14, 6, 205.25, 912

[56] References Cited

U.S. PATENT DOCUMENTS

| | | | |
|---|---|---|---|
| 3,859,995 | 1/1975 | Colston | 128/204.25 |
| 4,265,237 | 5/1981 | Schwanbom et al. | 128/204.25 |
| 4,351,328 | 9/1982 | Bodai | 128/207.15 |
| 4,506,665 | 3/1985 | Andrews et al. | 128/205.25 |

FOREIGN PATENT DOCUMENTS 54714 6/1982 European Pat. Off. ....... 128/207.15

Primary Examiner—Henry J. Recla
Attorney, Agent, or Firm—McGlew and Tuttle

[57] ABSTRACT

An attachment for the breathing gas supply during a high-frequency artificial respiration is connected to a ring conduit part in which the ventilation gas circulates. The attachment also comprises a patient connection part and a flow part connecting ring conduit part and patient part together. The parts are connected to each other by snap arms or rings. An injector nozzle and an ejector nozzle are mounted in the respective front walls of ring conduit part and patient connection part, in alignment with the apertures of the flow part which are designed as a collecting nozzle. The parts are sealed with each other by rings.

4 Claims, 2 Drawing Figures

ATTACHMENT FOR THE SUPPLY OF BREATHING GAS FOR HIGH-FREQUENCY ARTIFICIAL RESPIRATION

FIELD AND BACKGROUND OF THE INVENTION

This invention relates in general to respirators and in particular to a new and useful attachment for supplying breathing gas to a patient, An attachment similar to the invention is disclosed in German Pat. No. 33 13 855 relating to a system of high-frequency ventilation of patients. In a ring conduit, breathable ventilation gas is circulated. The attachment is connected to the ring conduit by one side through a supply connection and a discharge connection in such a way that the ventilating gas flows through the inner space of the attachment. On the other side, this inner space is connected to a tracheal tube, thus to the patient. The inner space is divided by a flow guide into partial spaces. The flow guide is designed as a two-side collecting nozzle which is associated at either side with an injector nozzle. Both the injector nozzles project through the wall of the guide to the space center as slender tubes which are angled at their ends. They are connected to a breathing gas source. The injector nozzle at the ring conduit side protrudes through the attachment into the tracheal tube axially. In an inspiration phase, it operates as a jet nozzle at high frequency pulses and, along with the jet breathing gas, supplies the patient with fresh ventilating gas taken by suction from the ring conduit. The injector nozzle at the tracheal tube side protrudes through the attachment axially to the ring conduit. It operates as an ejector nozzle and takes in breathing gas from the lungs and discharges it into the ring conduit. This prior art attachment is in a single piece, thus not easy to manufacture. The injector nozzles projecting into the free cross sectional area are disturbing during a cleaning process and the supply and discharge connections cannot be adapted, for example by turning, to suitable positions relative to the patient.

SUMMARY OF THE INVENTION

The present invention is directed to an attachment for supplying breathing gases to a person in which the prior art drawbacks are eliminated and which, primarily, can be cleaned without exposing the important injector nozzles to damage, and are easily adaptable to variations in position relative to the patient.

In accordance with the invention, an attachment for supplying breathing gas to a patient during high-frequency artificial respiration comprises a central tubular flow part, a ring conduit part which as a tubular portion engaged over a portion of the adjacent end of the tubular flow part and a supply conduit part having a delivery conduit and a tubular portion engaged over an opposite end portion of the tubular flow part.

Accordingly it is an object of the invention to provide an improved attachment for supplying breathing gas to a patient which includes an assembly of three parts with two end parts engaged over a tubular portion of a central part, one end part providing a means for supplying a breathing gas and having a delivery connection to the patient and the opposite end part having a closable connection at one end and a connection for connecting the tube to a patient at its opposite end through an endotracheal tube, for example.

Some particular advantages of the invention are the easy assemblage of three separate parts which, therefore, not only can be easily manufactured, but also can be assembled and disassembled and cleaned in a simple way, since the injector and ejector nozzles are enclosed in the front walls of the tubular portions. There is no risk of bending or even breaking the nozzles, and thus making them inoperative in their important function which is difficult to check. By turning the parts of the attachment relative to each other, any adaptation in position is possible.

A further object of the invention is to provide an apparatus for use in respiration particularly high-frequency artificial respiration which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
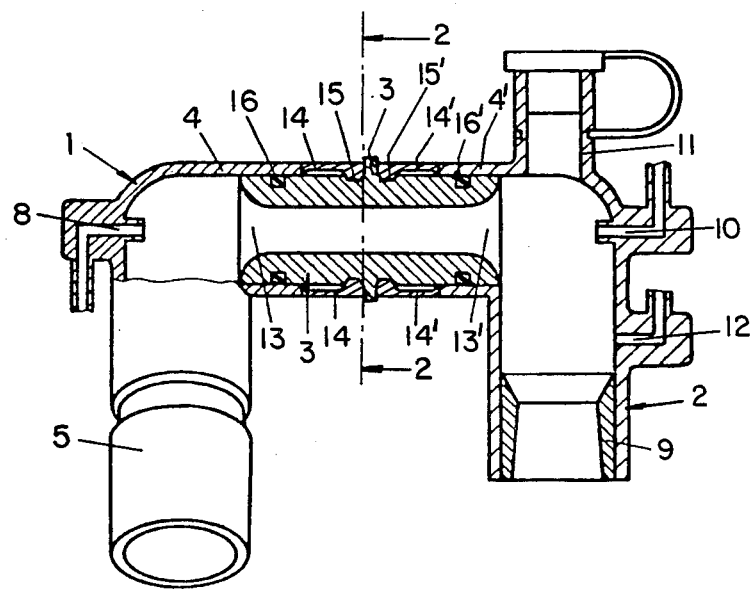
FIG. 1 is a longitudinal sectional view of an attachment, constructed in accordance with the invention.
Figure 2:
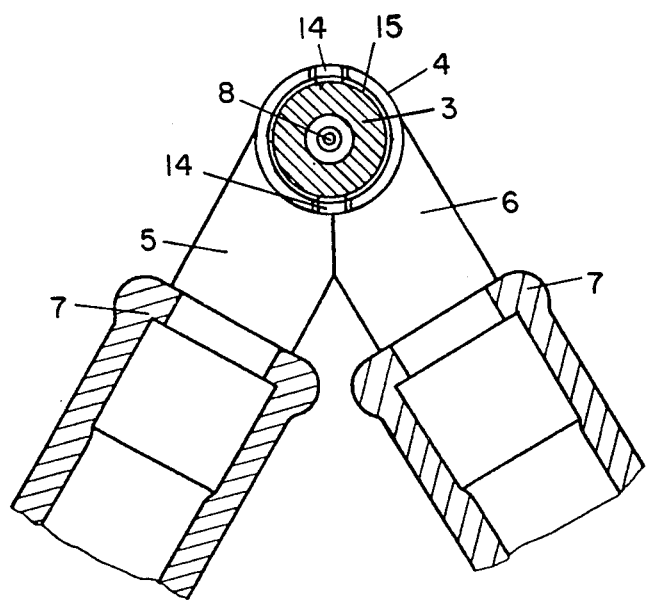
FIG. 2 is a cross sectional view taken along line 2—2 of FIG. 1.

Referring to the drawings in particular invention embodied therein comprises an attachment for supplying breathing gas to a patient during high frequency artificial respiration which comprises a central tubular flow part generally designated 3, a ring conduit part generally designated 1 and a patient connection part generally designated 2. The ring conduit part 1 has a tubular portion or part 4 engaged over a portion adjacent one end of the central tubular flow part 3. In addition, the ring conduit part 1 includes a supply conduit having a respirator gas supply conduit 5 and a breathing gas delivery conduit 6 each rotatably connected to the tubular portion 4. The patient connection part 2 has a patient connection part tubular portion 4' which is engaged over an opposite end of the central tubular flow part and it has a closable connection 11 at its one end and a cone connection 9 at its opposite end.

The attachment comprises a ring conduit part 1, a patient connection part 2, and a flow part 3 connecting the two other parts to one another.

The ring conduit part 1 comprises a tubular portion 4 and, extending at right angles thereto, a supply connection 5, and a discharge connection 6. The two connections 5 and 6 form an acute angle with each other and are to be engaged by flexible tubes 7,7 to establish connections with the ring conduit system. An injector nozzle 8 is mounted in the front wall of tubular portion 4 and extends axially toward flow part 3. The nozzle 8 is supplied from a breathing gas source.

Patient part 2 comprises a tubular portion 4' designed identically with the tubular portion 4 of part 1, but in an assembled state it extends in an opposite direction. A standard cone connector 9 extends from the tubular portion 4' at right angles, to establish a connection to the patient through an endotracheal tube (not shown), for example. An ejector nozzle 10 is mounted in the front wall of the tubular portion 4' and it is connected to a breathing gas source and extends axially toward flow part 3. A closable similar connection 11 is provided for the introduction of a suction catheter (not shown). The respiratory tract pressure can be sensed through a connection 12.

Flow part 3 performs the function of a collecting nozzle for injector nozzle 8 and ejector nozzle 10 and, at the same time connects ring conduit part 1 to patient part 2. The three parts, however, are pivotable relative to each other. Flow part 3 is symmetrical in shape and its flow passages 13 at the two sides are identical in design.

The three parts 1, 2 and 3 are connected to each other through snap arms or rings 14, 14' which are provided on tubular portions 4, 4' to engage circular grooves 15, 15' on flow part 3. The parts 1, 2 and 3 are sealed against each other by seal rings 16, 16' permitting the mutual pivotal motion of the parts.

While specific embodiments of the invention have been shown and described in detail to illustrate the application of the principles of the invention, it will be understood that the invention may be embodied otherwise without departing from such principles.

What is claimed is:

1. An attachment for supplying breathing gas to a patient during high-frequency artificial respiration, comprising a central tubular flow part having opposite open ends and defining oppositely extending collecting nozzles therein, a ring conduit part having a first tubular portion mounted over a portion of said tubular flow part adjacent its one end thereof, said ring port having an opposite tubular end portion divided into a supply connection adapted to be connected to a respiratory gas supply conduit and a discharge connection adapted to be connected to a delivery conduit, said supply and discharge connections each being rotatably connected over said opposite tubular end portion, a patient connection tube having a first tubular end portion mounted over the opposite end of said central tubular flow part and an opposite tubular end portion adapted to be connected to a patient's respiratory system, a first injector nozzle for breathing gas connected into said ring conduit part and directed toward and in alignment with the collecting nozzle in said central tubular flow part, and a second injector nozzle for breathing gas connected into said patient connection tube and directed toward and in alignment with the collecting nozzle in said central tubular flow part such that said first and second nozzles are directed toward each other; and said central tubular flow part having a pair of annular grooves on the outer surface thereof, said first tubular end portions of said ring conduit part and patient connection tube each having snap arms extending therefrom and each engaged in one of said annular grooves.

2. An attachment according to claim 1, wherein said supply conduit connection and said delivery conduit connection form an acute angle between each other and extend substantially at a right angle to said central tubular flow part.

3. An attachment according to claim 1, wherein said patient connection tube includes one end having a closable part and an opposite end having a cone connector.

4. An attachment according to claim 3, wherein said patient connector tube is provided with a connection for sensing the respiratory tract pressure.

* * * * *